US011744439B2

(12) United States Patent
Frangioni

(10) Patent No.: US 11,744,439 B2
(45) Date of Patent: Sep. 5, 2023

(54) MICRO CMOS SCOPES FOR MEDICAL IMAGING

(71) Applicant: Curadel, LLC, Natick, MA (US)

(72) Inventor: John V. Frangioni, Weston, MA (US)

(73) Assignee: Curadel, LLC, Natick, MA (US)

(*) Notice: Subject to any disclaimer, the term of this patent is extended or adjusted under 35 U.S.C. 154(b) by 0 days.

(21) Appl. No.: 17/840,748

(22) Filed: Jun. 15, 2022

(65) Prior Publication Data
US 2022/0346628 A1 Nov. 3, 2022

Related U.S. Application Data

(63) Continuation of application No. 16/372,504, filed on Apr. 2, 2019, now Pat. No. 11,382,487.

(60) Provisional application No. 62/651,921, filed on Apr. 3, 2018.

(51) Int. Cl.
A61B 1/00 (2006.01)
A61B 1/05 (2006.01)
A61B 1/04 (2006.01)
H01L 27/092 (2006.01)
H04N 5/33 (2023.01)

(52) U.S. Cl.
CPC .... *A61B 1/000094* (2022.02); *A61B 1/00009* (2013.01); *A61B 1/0019* (2013.01); *A61B 1/046* (2022.02); *A61B 1/05* (2013.01); *H01L 27/0922* (2013.01); *H04N 5/33* (2013.01)

(58) Field of Classification Search
CPC ........... A61B 1/04; A61B 1/042; A61B 1/043; A61B 1/046; A61B 1/05; A61B 1/051; A61B 1/053
See application file for complete search history.

(56) References Cited

U.S. PATENT DOCUMENTS

| | | | |
|---|---|---|---|
| 5,517,997 A * | 5/1996 | Fontenot | A61B 90/36 600/476 |
| 5,594,497 A | 1/1997 | Ahern et al. | |
| 5,797,837 A | 8/1998 | Minami | |
| 5,827,190 A | 10/1998 | Palcic et al. | |
| 6,652,452 B1 | 11/2003 | Seifert et al. | |
| 7,030,904 B2 | 4/2006 | Adair et al. | |
| 8,485,966 B2 | 7/2013 | Robertson | |
| 8,498,695 B2 | 7/2013 | Westwick et al. | |
| 2002/0035330 A1 | 3/2002 | Cline et al. | |
| 2011/0230719 A1* | 9/2011 | Katakura | A61B 1/0638 600/156 |
| 2013/0038689 A1 | 2/2013 | Mcdowall | |
| 2013/0116508 A1 | 5/2013 | Shida | |
| 2016/0051126 A1 | 2/2016 | Troller et al. | |
| 2016/0206202 A1 | 7/2016 | Frangioni | |
| 2016/0262602 A1 | 9/2016 | Yu | |

(Continued)

FOREIGN PATENT DOCUMENTS

CN 102727166 A 10/2012
CN 102749139 A 10/2012
(Continued)

Primary Examiner — Aaron B Fairchild
(74) Attorney, Agent, or Firm — Myers Bigel, P.A.

(57) ABSTRACT

In various embodiments, a scope-based imaging system is introduced. An optical sensor assembly located at the tip of the scope may include the CMOS sensors, filters, and lenses/mirrors, to perform fluorescence imaging using the scope.

13 Claims, 20 Drawing Sheets

(56) References Cited

U.S. PATENT DOCUMENTS

2016/0309992 A1 10/2016 Stith et al.
2017/0167980 A1* 6/2017 Dimitriadis .............. A61B 3/14

FOREIGN PATENT DOCUMENTS

CN 105852784 A 8/2016
DE 202011101011 U1 9/2011

* cited by examiner

MICRO CMOS SCOPES FOR MEDICAL IMAGING

RELATED APPLICATIONS

This application is a continuation of U.S. patent application Ser. No. 16/372,504, filed Apr. 2, 2019, which claims priority to U.S. Provisional Patent Application No. 62/651,921, filed on Apr. 3, 2018, entitled "MICRO CMOS SCOPES FOR MEDICAL IMAGING" by Frangioni, the contents of each of which are incorporated by reference herein.

TECHNICAL FIELD

The present disclosure relates generally to imaging systems and, more particularly, to micro complementary metal-oxide-semiconductor (CMOS).

BACKGROUND

Various forms of imaging systems are used in the healthcare and research fields, today. In some cases, the imaging may be performed in vivo, i.e., within a living organism. Such imaging systems may include, for example, endoscopic imaging systems, laparoscopic imaging systems, open space imaging systems, and the like. In other cases, the imaging may be performed ex vivo, such as in the case of imaging biopsied tissue.

In a conventional surgical scope, the optical image must be relayed from the tip of the scope to the opposite end, where a camera or eyepiece can capture the image. There are many techniques for relaying, including multiple lens sets, gradient index lenses, and coherent fiber bundles. However, all of them result in tremendous loss of light due to absorption and scattering or image degradation. In fact, a conventional laparoscope might require 40 lenses to properly relay the image from the tip to the camera, and even if there is only 1% loss at every lens, only ⅔ of the starting light is transmitted. Because of additional losses inherent in multi-lens systems, the actual light transmitted is typically a small fraction of the total light available, requiring extremely powerful illumination to create an image capable of being imaged.

BRIEF DESCRIPTION OF THE DRAWINGS

The embodiments herein may be better understood by referring to the following description in conjunction with the accompanying drawings in which like reference numerals indicate identically or functionally similar elements, of which.

Figure 1:
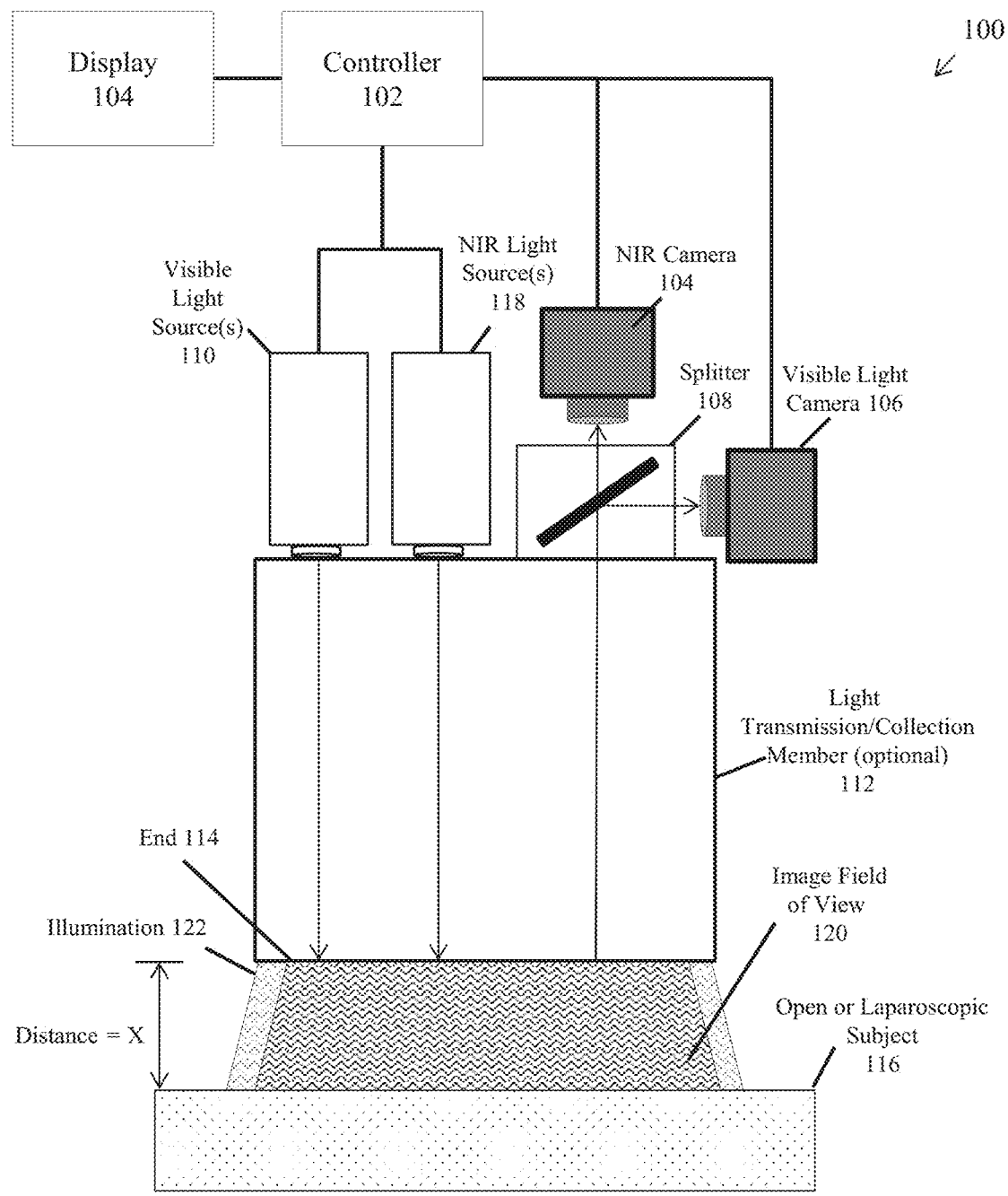
FIG. 1 shows an example embodiment of an imaging system.

In the figures, reference numbers refer to the same or equivalent parts of the present invention throughout the several figures of the drawing.

SUMMARY

According to the techniques described herein, an imaging system is disclosed. In some embodiments, the imaging system includes an optical sensor assembly at the tip of a medical scope. The sensor assembly includes micro complementary metal-oxide-semiconductor (CMOS) sensors, filters, and lenses that allows for the performance of fluorescence imaging using the scope. In various embodiments, the scope may utilize a 2-sensor configuration whereby the subject of the imaging is imaged using both visible light and near-infrared (NIR). In other embodiments, a 3-sensor scope configuration is disclosed, whereby the subject can be imaged using visible light and NIR light at two different wavelengths.

DETAILED DESCRIPTION

To provide an overall understanding of the invention, certain illustrative embodiments will now be described, including a system for generating superimposed circulatory and tissue images in video format. However, it will be understood that the methods and systems described herein can be suitably adapted to other medical imaging applications where visible light tissue images may be usefully displayed with diagnostic image information obtained from outside the visible light range and superimposed onto the visible light image. More generally, the methods and systems described herein may be adapted to any imaging application where a visible light image may be usefully displayed with a superimposed image captured from areas within the visible light image that are functionally marked to emit photons outside the visible light range by a dye or other material. For example, the systems and methods are applicable to a wide range of diagnostic or surgical applications where a target pathology, tissue type, or cell may be labeled with a fluorescent dye or other fluorescent substance. These and other applications of the systems described herein are intended to fall within the scope of the invention.

FIG. 1 shows an embodiment of an imaging system that may be used, for example, to image tissue either in vivo or ex vivo. The imaging system 100 may generally include a controller 102, a display 104, a near-infrared (NIR) camera 104, one or more NIR light sources 118, a visible light camera 106, a splitter mechanism 108, one or more visible light sources 110, and/or a light transmission/collection member 112. As would be appreciated, imaging system 100 may be adapted for any number of uses including, but not limited to, open surgical imaging, endoscopic or laparoscopic imaging, block face imaging (e.g., of a tissue sample), or the like. Examples of imaging system 100 include the FLARE® (FLuorescence-Assisted Resection and Exploration) imaging systems available from Curadel LLC, Marlborough, Mass., as well as any other type of optical imaging system.

In various embodiments, imaging system 100 may be configured to capture fluorescence images of a subject 116, such as organic tissue, using its cameras 104, 106. Prior to imaging subject 116 and/or during the imaging by imaging system 100, subject 116 may be injected with a fluorescent dye (e.g., a fluorophore) that is optically reactive when exposed to certain wavelengths of light. Generally, subject 116 may be any form of organic tissue in an open or laparoscopic/endoscopic setting, in various embodiments. For example, some dyes may be photo-reactive in the NIR range and emit light when exposed to illumination in this range (e.g., by an NIR light source 118). Leveraging this, imaging system 100 may capture contrasting images of subject 116 with NIR camera 104 capturing the phosphorescence/NIR images of subject 116 and the dye infused therein, and visible light camera 106 capturing visible light images of subject 116. In general, near-infrared as used herein refers to the range of wavelengths between 660-900 nanometers ("nm").

Generally, and as described in more detail below, controller 102 may provide electronic control over visible light source(s) 110, NIR light source(s) 118, and cameras 104, 106, to capture the NIR and visible light images of subject 116, respectively. Controller 102 may also, in some embodiments, combine the imaging data from both types of captured images into a combined image. For example, such a combined image may present the NIR/fluorescence image data as an overlay for the visible image data, thereby providing a visual indication of the locations within subject 116 where the fluorescent dye is located. For example, certain dyes may bind to specific tumors, thereby facilitating visualization of the tumor within subject 116. In another example, such a dye may be injected into the blood stream of a live patient, thereby allowing the user of imaging system 100 to visualize the diffusing of the dye within subject 116. Once the NIR and visible light image data has been processed, controller 102 may provide the processed image data to a local or remote (e.g., connected via a network) display 104 for visualization and review by a user.

In some embodiments, visible light source(s) 110 may include a visible light source that serves as a light source for visible light camera 106. For example, the visible light source 110 may be, for example, a near-infrared depleted white light source. Notably, this may be a one-hundred and fifty Watt halogen lamp with one or more filters to deplete wavelengths greater than 700 nm. Generally, any light source constrained to wavelengths between 400 nm and 700 nm may operate as the visible light source in light source(s) 110. In further embodiments, however, ambient lighting in the area may be used in part, or in whole, to provide the visible illumination to subject 116.

In some cases, imaging system 100 may be surrounded by an operating area (not shown) closed to ambient light. As will become clear from the following, many visible light sources such as incandescent lamps, halogen lamps, or daylight may include a broad spectrum of electromagnetic radiation that extends beyond the range of visible light detected by the human eye and into wavelengths used in the present system as a separate optical channel for generating diagnostic images. In order to effectively detect emission in these super-visible light wavelengths, it is preferred to enclose the surgical field, light source(s) 110, 118 and cameras 104, 106 in an area that is not exposed to broadband light sources. This may be achieved by using an operating room closed to external light sources, or by using a hood or other enclosure or covering for the surgical field that prevents invasion by unwanted spectrum. The visible light source of illumination light source(s) 110 may then serve as a light source for the visible light camera 106, and also for provide conventional lighting within the visible light spectrum. As used herein, the term "operating area" is intended specifically to refer to an open surgical site that is closed to ambient light. Endoscopic or laparoscopic applications, as described below, are confined to surgical procedures within a closed body cavity, and do not include an operating area as that term is intended herein.

In addition to capturing visible light images of subject 116, NIR camera 104 of imaging system 100 may capture NIR images of subject 116 (and the dye present therein) as illuminated by an excitation NIR light source 118. For example, in certain applications, the excitation light source and resulting emission from the dye present in subject 116 may have wavelengths near or below 700 nm, as with Cy5 dye, which emits light when excited at 650 nm. These near-red dyes may be used with the present system, however, this requires a visible light source that excludes a portion of the visible light spectrum in which the dye operates, i.e., a far-red depleted white light source. Similarly, applications using quantum dots as a fluorescent substance may have absorption or emission wavelengths anywhere in the visible light spectrum, and a suitable visible light source should be depleted at the wavelength(s) of interest. As such, the visible light source should more generally be understood to be a source of light that includes some, but not necessarily all, of the wavelengths of visible light.

It should also be understood that, in a far-red imaging system or infrared imaging system such as those noted above, NIR camera 104 described in the example embodiment will instead be a camera sensitive to the emission wavelength of the injected dye or other fluorescent substance, and that other modifications to light sources, filters and other optics will be appropriate. Similar modifications may be made to isolate a band of wavelengths for dye excitation and emission anywhere within or outside the visible light range, provided that suitable optics, cameras, and dyes are available. Other fluorescent substances may also be used. For example, quantum dots may emit at visible light wavelengths, far-red, near-infrared, and infrared wavelengths, and at other wavelengths, typically in response to absorption below their emission wavelength. Suitable adjustments will be made to the excitation light source and the emission camera, the NIR camera in the example embodiment, for such applications. Cameras sensitive to far-red, near-infrared, and infrared wavelengths are commercially available.

In particular, NIR light source(s) 118 may include an excitation light source that provides light at a wavelength that excites the dye present in subject 116. This may be, for example, a laser diode such as a 771 nm, 250 mW laser diode system, which may be obtained from Laser Components of Santa Rosa, Calif. Other single wavelength, narrowband, or broadband light sources may be used, provided they do not interfere with the visible light image captured by visible light camera 106 (e.g., a video camera, etc.) or the emission wavelength of the dye. The near-infrared band is generally understood to include wavelengths between 700 nm and 1000 nm, and is a useful wavelength range for a number of readily available excitation light sources and dyes that may be used with the systems described herein. Suitable optical coupling and lenses may be provided to direct each of the visible light source and the excitation light source at an area of interest of subject 116.

Generally, splitter 108 may be operable to separate and direct the NIR and visible light received from the illuminated subject 116. For example, splitter 108 may include any number of filters and/or dichroic mirrors, to direct the fluorescence wavelengths towards NIR camera 104 and the visible wavelengths towards visible light camera 106 for capture. A number of arrangements of the cameras 104, 106 and splitter 108 are possible, and may involving reflecting or transmitting either the visible light image or the emission wavelength image.

In various embodiments, imaging system 100 may also include a light transmission/collection member 112 that conveys the light from light source(s) 110, 118 to the surface subject 116 and direct any light (e.g., reflected light, etc.) from subject 116 towards splitter 108 and cameras 104, 106. For example, light transmission/collection member 112 may include any number of fiber optics or other light guides/channels, to direct the illumination from light source(s) 110, 118 towards subject 116 and the captured light from subject 116 towards cameras 104, 106. In further embodiments, light source(s) 110 and/or 118 may be decoupled from light transmission/collection member 112, to provide illumination to subject 116 directly. In some embodiments, light transmission/collection member 112 may also include any number of lenses, to transmit light from light source(s) 110, 118 towards subject 116 and collect light from subject 116 for processing by cameras 104, 106.

Typically, the light provided by visible light source(s) 110 and from NIR light source(s) 118, which are described in greater detail below, may be transmitted via different channels within light transmission/collection member 112. In other embodiments, they may be mixed. Note, however, that light transmission/collection member 112 may be optional, in some embodiments. For example, while endoscopic, laparoscopic, etc. application may employ member 112, other implementations, such as open surgical, may not require member 112 and this component can be omitted.

NIR camera 104 may be any still or moving image camera suitable for capturing images at the emission wavelength of the excited dye present in subject 116. The near-infrared camera may be, for example, an Orca-ER near-infrared camera with settings of gain 7, 2×2 binning, 640×480 pixel field of view, and an exposure time of 20 ms and an effective frame rate of fifteen frames per second. The Orca-ER is commercially available from Hamamatsu Photonic Systems of Bridgewater, N.J. It will be understood that the NIR camera 104 in FIG. 1 is only an example. An infrared camera, a far-red camera, or some other camera or video device may be used to capture an emission wavelength image, with the camera and any associated filters selected according to the wavelength of a corresponding fluorescent substance used with the imaging system. As used herein, the term "emission wavelength camera" is intended to refer to any such camera that may be used with the systems described herein.

Visible light camera 106 may be any video camera suitable for capturing images of the surgical field 106 in the visible light spectrum. In further embodiments, the visible light camera 106 may instead be a camera configured to take still images, as opposed to video. In one embodiment, camera 106 is a color video camera model HV-D27, commercially available from Hitachi of Tarrytown, N.Y. For example, the video camera 106 may capture red-green-blue (RGB) images at thirty frames per second at a resolution of 640×480 pixels, or at any other number of frames or resolutions, as desired. In another example, camera 106 may be a high resolution Canon EOS 700 white light camera available from Canon, Melville, N.Y., although any other suitable white light camera can be used in other implementations. More generally, NIR camera 104 and visible light camera 106 may be any device capable of photonic detection and conversion to electronic images, including linear photodiode arrays, charge coupled device arrays, scanning photomultiplier tubes, and so forth.

Display 104 may be a television, high-definition television, computer monitor, or other display configured to receive and render signals from controller 102. In some embodiments, display 104 may be a monocular or binocular eyepiece of the surgical microscope, with the near-infrared image superimposed on the visible light image in the eyepiece. In another embodiment, the eyepiece may use direct optical coupling of the surgical field to the eyepiece for conventional microscopic viewing, with the near-infrared image projected onto the eyepiece using, for example, heads-up display technology.

Generally, the controller 102 should be capable of digital filtering, gain adjustment, color balancing, and/or any other conventional image processing functions. The image from the NIR camera 104 is also typically shifted into the visible light range for display at some prominent wavelength, e.g., a color distinct from the visible light colors of the captured and/or displayed image data from camera 106, so that a superimposed image will clearly depict the dye. The controller 102 may also perform image processing to combine the image from the NIR camera 104 and the visible light camera 106. Where the images are displayed side-by-side, this may simply entail rendering the images in suitable locations on a computer screen. Where the images are superimposed, a frame rate adjustment may be required. That is, if the visible light camera 106 is capturing images at the conventional rate of thirty frames per second and the NIR camera 104 is taking still pictures with an effective frame rate of fifteen frames per second, some additional processing may be required to render the superimposed images concurrently. This may entail either reducing the frame rate of the visible light camera 106 to the frame rate of the NIR camera 104 either by using every other frame of video data or averaging or otherwise interpolating video data to a slower frame rate. This may instead entail increasing the frame rate of the near-infrared image data, either by holding each frame of near-infrared data over successive frames of video data or extrapolating near-infrared data, such as by warping the near-infrared image according to changes in the video image or employing other known image processing techniques.

In one embodiment, a near-infrared depleted visible light source may be used as light source 110, the excitation light source (e.g., NIR light source 118) is a 760 nm, 2.5 W laser diode, the dye is indocyanine green or ZW800-1, and imaging system 100 includes a 780 nm dichroic mirror configured to transmit near-infrared light and reflect visible light, the a 781 nm longpass emission filter, and a 400 nm to 700 nm filter. The controller 102 comprises a processing circuit configured with software for image capture from the NIR camera 104 and the visible light camera 106, for making suitable color adjustment to the images from the NIR camera 104, for making frame rate adjustments to the visible light camera 106 image, and for combining the two images for superimposed display on the display 104.

The systems described above have numerous surgical applications. For example, the system may be deployed as an aid to cardiac surgery, where it may be used intraoperatively for direct visualization of cardiac blood flow, for direct visualization of myocardium at risk for infarction, and for image-guided placement of gene therapy and other medicinals to areas of interest. The system may be deployed as an aid to oncological surgery, where it may be used for direct visualization of tumor cells in a surgical field or for image-guided placement of gene therapy and other medicinals to an area of interest. The system may be deployed as an aid to general surgery for direct visualization of any function amenable to imaging with fluorescent dyes, including blood flow and tissue viability. In dermatology, the system may be used for sensitive detection of malignant cells or other skin conditions, and for non-surgical diagnosis of dermatological diseases using near-infrared ligands and/or antibodies.

In further embodiments, imaging system 100 may be adapted for use in an endoscope or laparoscope. Typically, a laparoscope is inserted into a body cavity through an incision, as distinguished from an endoscope which is inserted through an existing body opening such as the throat or rectum. A laparoscope has a different form factor than an endoscope, including different dimensional requirements. Furthermore, use of a laparoscope involves at least one additional step of making an incision into a body so that the laparoscope may be inserted into a body cavity. It will further be appreciated that the imaging system 100 may be used to simplify imaging devices other than endoscopes and laparoscopes, such as by providing an integrated, coaxial illumination and image capture device using the techniques described above.

Figure 2:
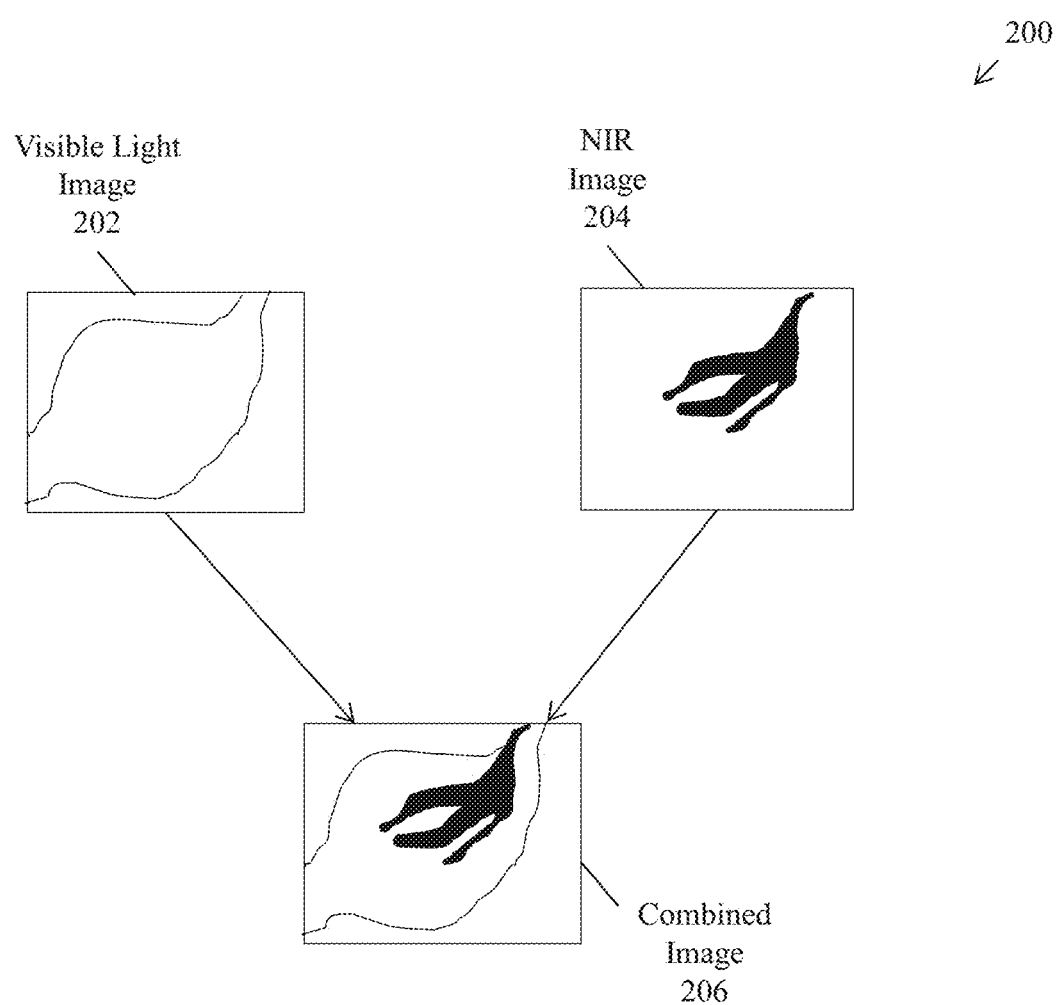
FIG. 2 shows the combination of visible and fluorescence images.

FIG. 2 shows an image displaying both a circulatory system and surrounding tissue. As described above, a visible light tissue image 202 is captured of tissue within a surgical field. As noted above, the visible light tissue image 202 may include a subset of visible light wavelengths when an optical channel for dye imaging includes a wavelength within the visible light range. A near-infrared image 204 is also captured of the same (or an overlapping) field of view of the surgical field. Although referred to here for convenience as a near-infrared image, it should be clear that the dye-based image 204 may also, or instead, employ other wavelengths, such as far-red or infrared wavelengths. The near-infrared image 204 may be shifted to a visible wavelength for display, preferably using a color that is prominent when superimposed on the visible light tissue image 202. The images 402, 404 may be frame-rate adjusted as appropriate for video display of the surgical field.

The images may be displayed separately as the visible light tissue image 202 and the near-infrared image 204. Or the images 202, 204 may be combined into a combined image 206 by the image processing unit described above. The combined image 206 may then be used as an aid to the procedures described above, or to any other surgical or diagnostic procedure that might benefit from the dye-based imaging techniques described herein.

Figure 3:
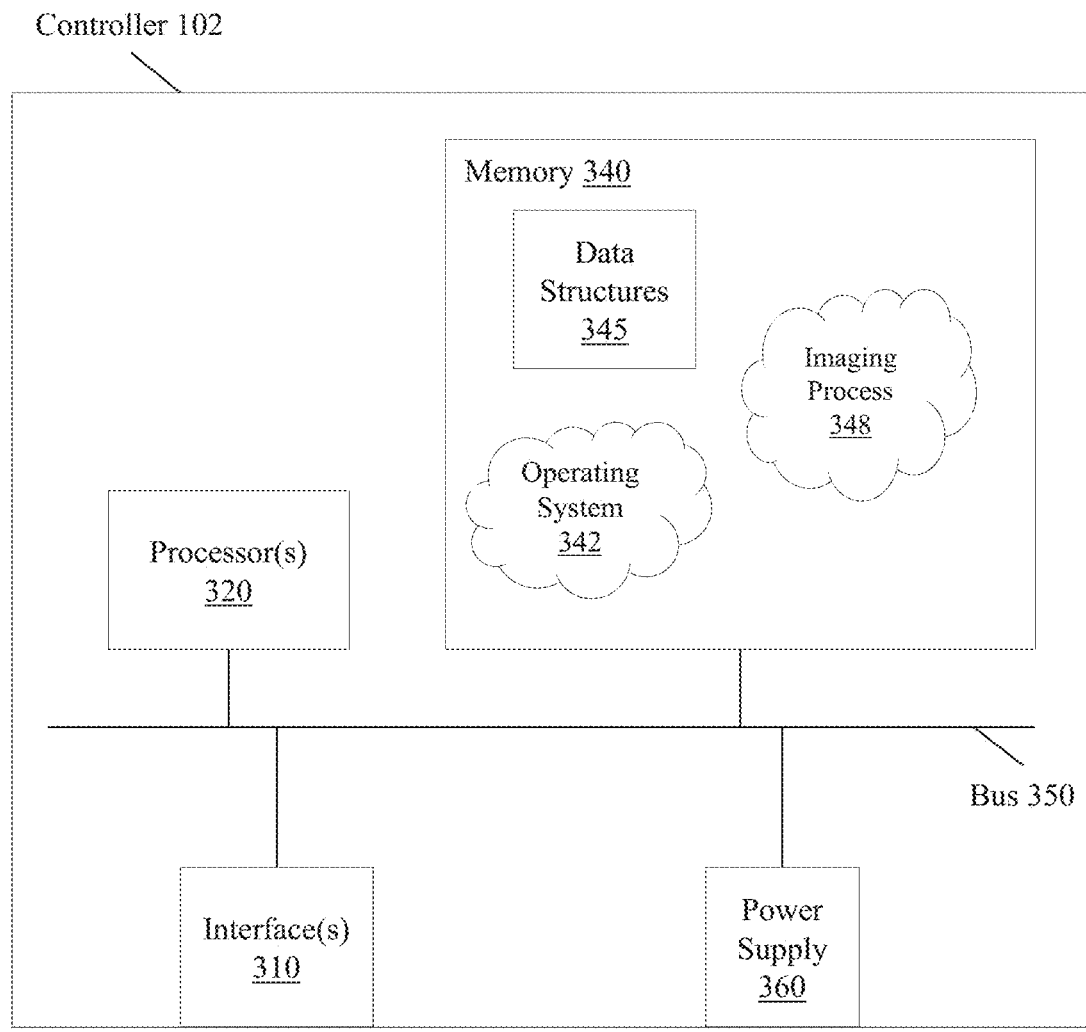
FIG. 3 illustrates an example controller for an imaging system.

FIG. 3 illustrates a controller 102 that may be used as part of any of the imaging systems/devices described herein, according to various embodiments. As shown, controller 102 may comprise one or more network interfaces 310 (e.g., wired, wireless, etc.), at least one processor 320, and a memory 340 interconnected by a system bus 350, as well as a power supply 360 that provides electrical power to controller 102.

The interface(s) 310 contain the mechanical, electrical, and signaling circuitry for communicating data with other components of the imaging device/system and/or with other computing devices (e.g., via a computer network). For example, interface(s) 310 may be configured to transmit and/or receive data using a variety of different communication protocols via a communication network (e.g., to upload image data to a cloud service, to download software or data updates, etc.). In further examples, interface(s) 310 may be coupled to the various components of the imaging device to provide control commands to the camera(s), lighting source(s), etc., of the imaging device and/or to receive captured image data from the camera(s). Interface(s) 310 may also be in communication with an electronic display to display the resulting images after processing.

The memory 340 comprises a plurality of storage locations that are addressable by the processor 320 and the network interfaces 310 for storing software programs and data structures associated with the embodiments described herein. The processor 320 may comprise hardware elements or hardware logic adapted to execute the software programs and manipulate the data structures 345. An operating system 342, portions of which are typically resident in memory 340 and executed by the processor 320, functionally organizes the device by, inter alia, invoking operations in support of software processes and/or services executing on the device. These software processes and/or services may comprise an imaging process 348, as described herein.

It will be apparent to those skilled in the art that other processor and memory types, including various computer-readable media, may be used to store and execute program instructions pertaining to the techniques described herein. Also, while the description illustrates various processes, it is expressly contemplated that various processes may be embodied as modules configured to operate in accordance with the techniques herein (e.g., according to the functionality of a similar process). Further, where certain processes have been shown separately, those skilled in the art will appreciate that processes may be routines or modules within other processes.

Imaging process 348, when executed by processor(s) 320, may be operable to perform any of the imaging functions described herein. For example, imaging process 348 may provide control over the components of the imaging device, to capture both color and fluorescence image data regarding organic tissue of interest. In turn, imaging process 348 may process the captured image data to form display data for display by an electronic display. For example, imaging process 348 may combine both the color and fluorescence data into an overlay image for display by the electronic display. Such a displayed image may be fully in color or at least partially in black and white or grayscale, in various embodiments.

As noted above, in a conventional surgical scope, the optical image must be relayed from the tip of the scope to the opposite end, where a camera or eyepiece can capture the image. There are many techniques for relaying, including multiple lens sets, gradient index lenses, and coherent fiber bundles. However, all of them result in tremendous loss of light due to absorption and scattering or image degradation. In fact, a conventional laparoscope might require 40 lenses to properly relay the image from the tip to the camera, and even if there is only 1% loss at every lens, only ⅔ of the starting light is transmitted. Because of additional losses inherent in multi-lens systems, the actual light transmitted is typically a small fraction of the total light available, requiring extremely powerful illumination to create an image capable of being imaged.

Figure 4A:
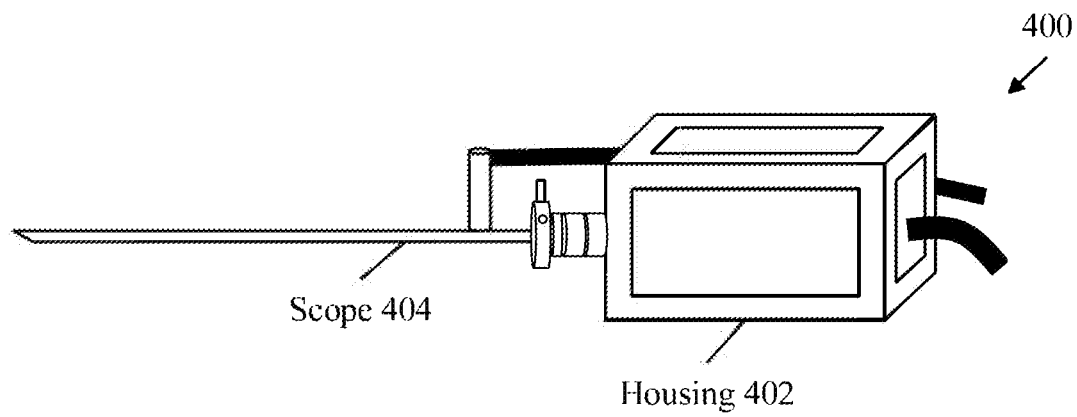
FIGS. 4A-4B illustrate an example scope-based imaging system.
Figure 4B:
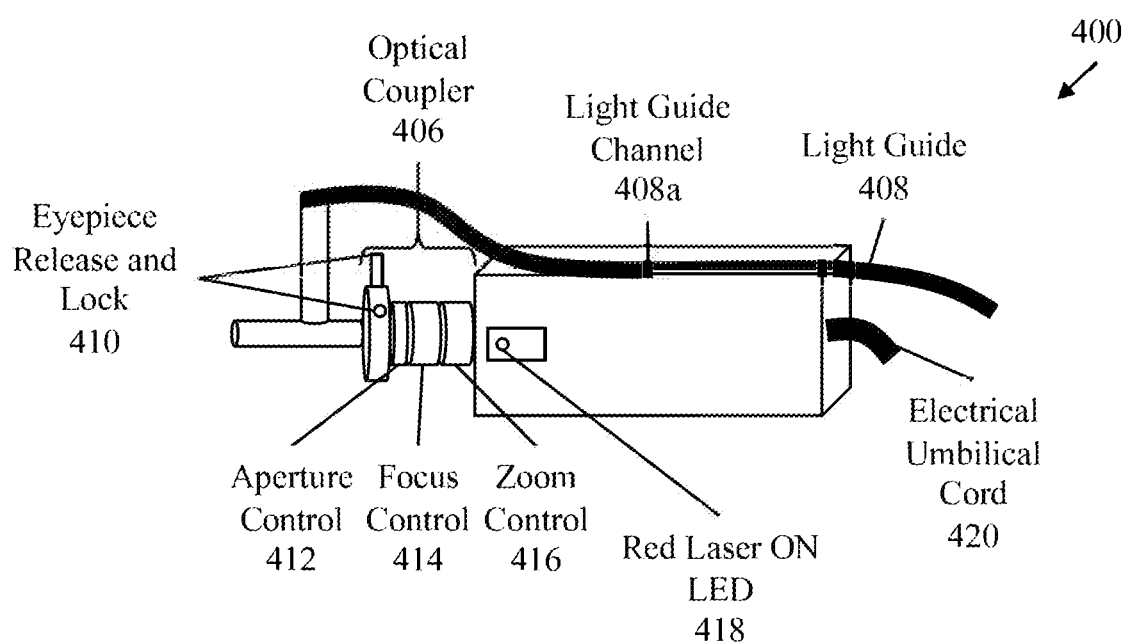

The imaging techniques described above allow for the simultaneous acquisition of color video and one or more channels of NIR fluorescent light, is a particularly difficult application because it requires that the relay system also be aberration corrected from approximately 400-900 nm, and highly transmissive over this wavelength range, as well. This, in turn, further increases complexity and cost of a scope-based imaging system. FIGS. 4A-4B illustrate example scope-based imaging system 400 that can be used for minimally invasive surgery (MIS). FIG. 4A shows system 400 with housing 402 and FIG. 4B shows system 400 with housing 402 removed. As shown, imaging system 400 includes an NIR-compatible scope 404, a separate light guide 408 forming a light guide channel 408a, a lens system (optical coupler 404) to couple the scope 404 to the camera, and a multi-channel camera (e.g., a FLARE® camera or other camera in accordance with the teachings herein) powered by electrical umbilical cord 420. User controls for system 400 may include an eyepiece release and lock 410, aperture control 412, focus control 414, zoom control 416, and/or a red laser ON LED 418.

Manufacturers have been moving towards integrated scope/cameras, where the camera is a physical part of the scope, which eliminates the optical coupler, as well as to "chip on tip" cameras that place the lensing and image sensor at the very end of the scope. In various embodiments, techniques are disclosed herein to perform fluorescence imaging during MIS, which includes a 2- or 3-sensor optical frame onto which is mounted the dichroic mirrors, filters, and lensing necessary to create a complete fluoroscopic imaging system. By decoupling the optics from the electronics using these techniques, MIS scopes of any diameter can be constructed, at any length, and/or with additional working channels, all while doing true fluorescence imaging via the scope.

In some cases, an entire family of MIS scopes can be constructed using the techniques herein, all utilize the same grip handle, silicone outer cover, electronics, and/or optical sensor frame. The main stainless steel tube is interchangeable for any diameter from 6 mm to 10 mm, permitting the addition of working channels or accessory ports to the larger diameter tubes. The system can also accommodate either 2-sensor (color and shared NIR 1/NIR 2 channels) or 3-sensor (separate color, NIR 1, and NIR 2 channels) tip optics, as desired.

Figure 5A:
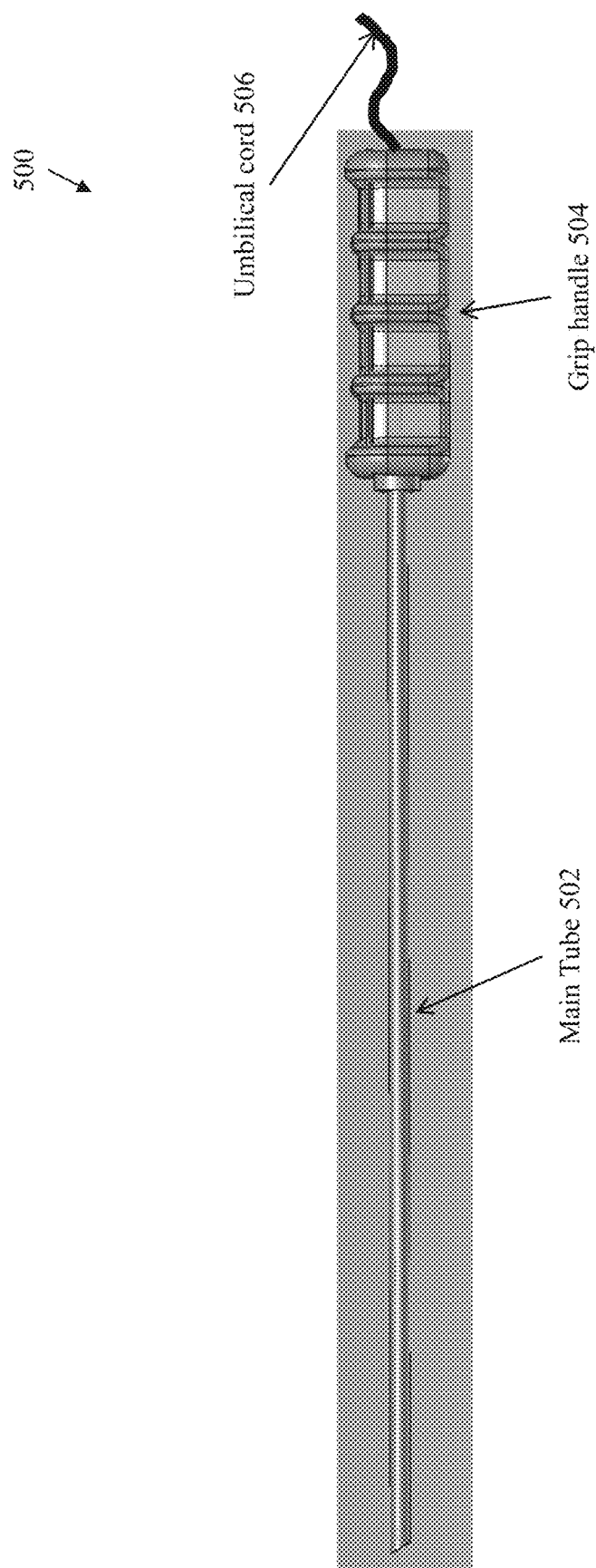
FIGS. 5A-5B illustrate schematic views of a scope-based imaging system.
Figure 5B:
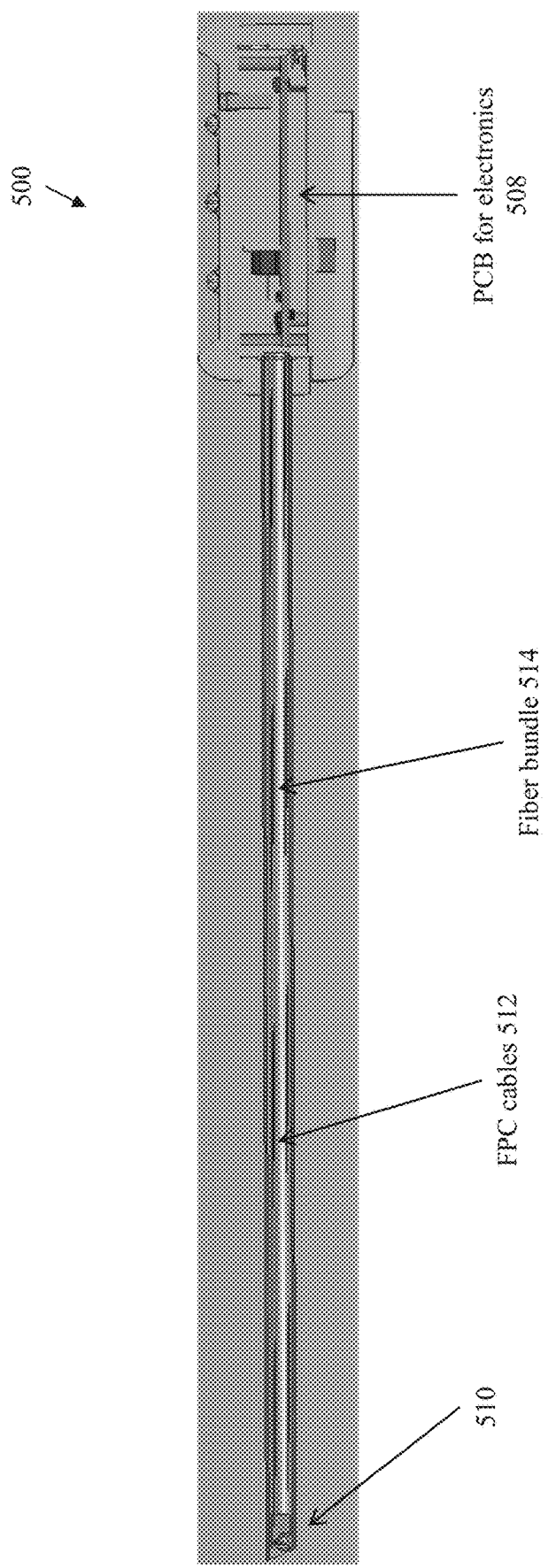

FIGS. 5A-5B illustrate such scopes in greater detail. As shown in FIG. 5A, scope 500 may comprise a main tube 502 (e.g., a stainless steel tube of any desired length), a grip handle 504 from which main tube 502 protrudes that may include an external, silicone cover, in some cases, and an umbilical cord 506. Umbilical cord 506 may include the electrical cabling (e.g., power, data, and/or control) and fiber bundle for illumination by scope 500. As shown in FIG. 5B, internal to grip handle 504 may be a printed circuit board (PCB) 508 for the electronics. In addition, at the tip/distal end of main tube 502 may be a scope tip assembly 510 comprising an optics frame, sensors, filters, and lenses. Internal to main tube 502 may also be FPC cables 512 connecting each sensor of assembly 510 to PCB 508 and fiber bundle 514 used to provide illumination via assembly 510 and potentially range finding capabilities, as well.

As a reminder, typical fluorescence imaging using the techniques herein utilizes the following excitation and light collection wavelengths:

TABLE 1

| Type | Illumination | Light Collection |
|---|---|---|
| Color Video | 400-650 nm | 400-650 nm |
| NIR Channel 1 (NIR 1) | 665 ± 2 nm laser | 685-735 nm |
| NIR Channel 2 (NIR 2) | 760 ± 2 nm laser | ≥781 nm |

All illumination wavelengths are pre-mixed using a custom light mixing system so that they can travel down the same fiber bundle to the scope. For 3-sensor scopes, each sensor is assigned to one of the light collection wavelength bands above. For 2-sensor scopes, the NIR 1 and NIR 2 channels are shared by a single sensor. This is accomplished by sequential toggling of the NIR 1 and NIR 2 lasers, and the use of a double-bandpass, dichroic mirror and double-bandpass, emission filter in front of the NIR sensor:

TABLE 2

| Type | Illumination | Light Collection |
|---|---|---|
| Color Video | 400-650 nm | 400-650 nm |
| NIR Channel 1 or 2 | 665 ± 2 nm OR 760 ± 2 nm laser | 685-735 nm and ≥781 nm |

As noted, the MIS scope introduced herein can accommodate either 2-sensor or 3-sensor configurations.

Figure 6:
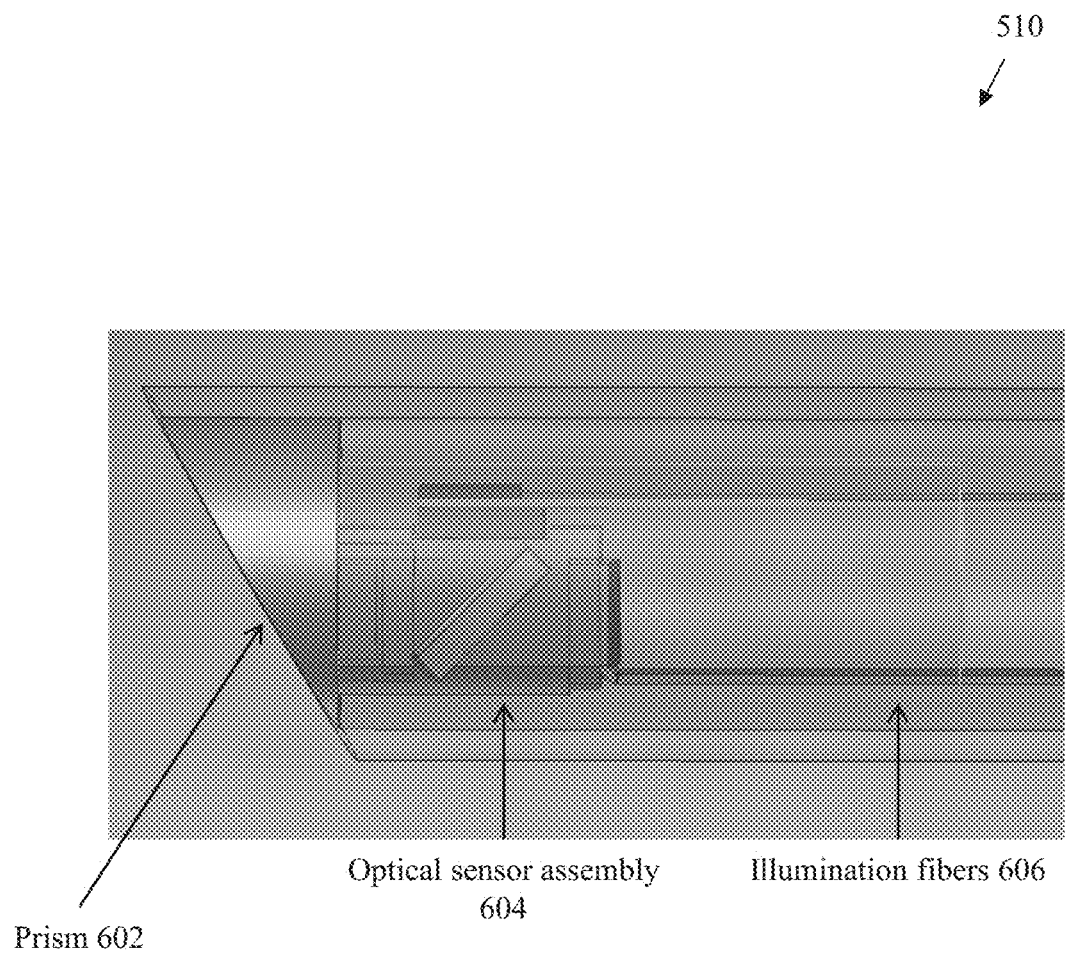
FIG. 6 illustrates an example scope tip assembly.

FIG. 6 illustrates an example scope tip assembly 510, according to various embodiments. In particular, a scope tip for a 2-sensor configuration is shown. However, a 3-sensor configuration is also possible, as detailed below. As shown, tip assembly 510 may comprise a prism 602 for angles other than zero degrees, an optical sensor assembly 604 (e.g., CMOS sensors, filters, and lens), and illumination fibers 606 on either side of optical sensor assembly 604.

Figure 7A:
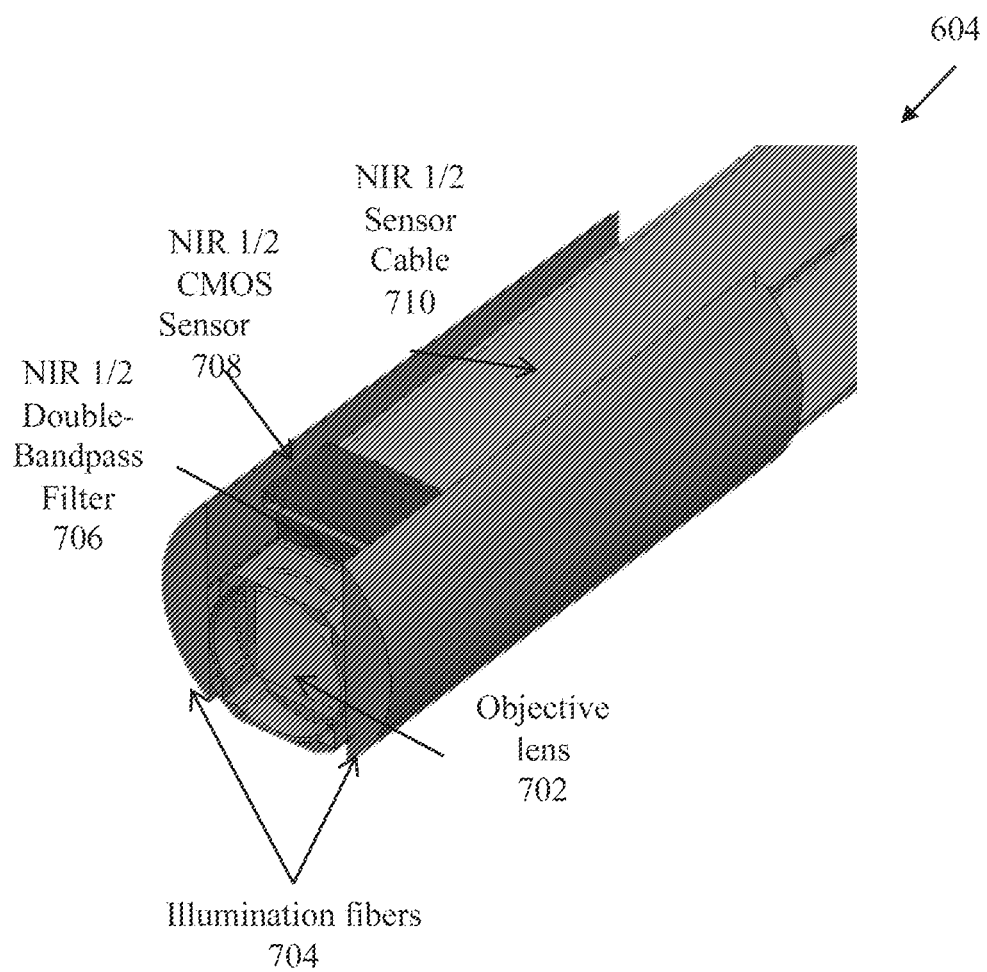
FIGS. 7A-7C illustrate example views of a 2-sensor optical sensor assembly.
Figure 7B:
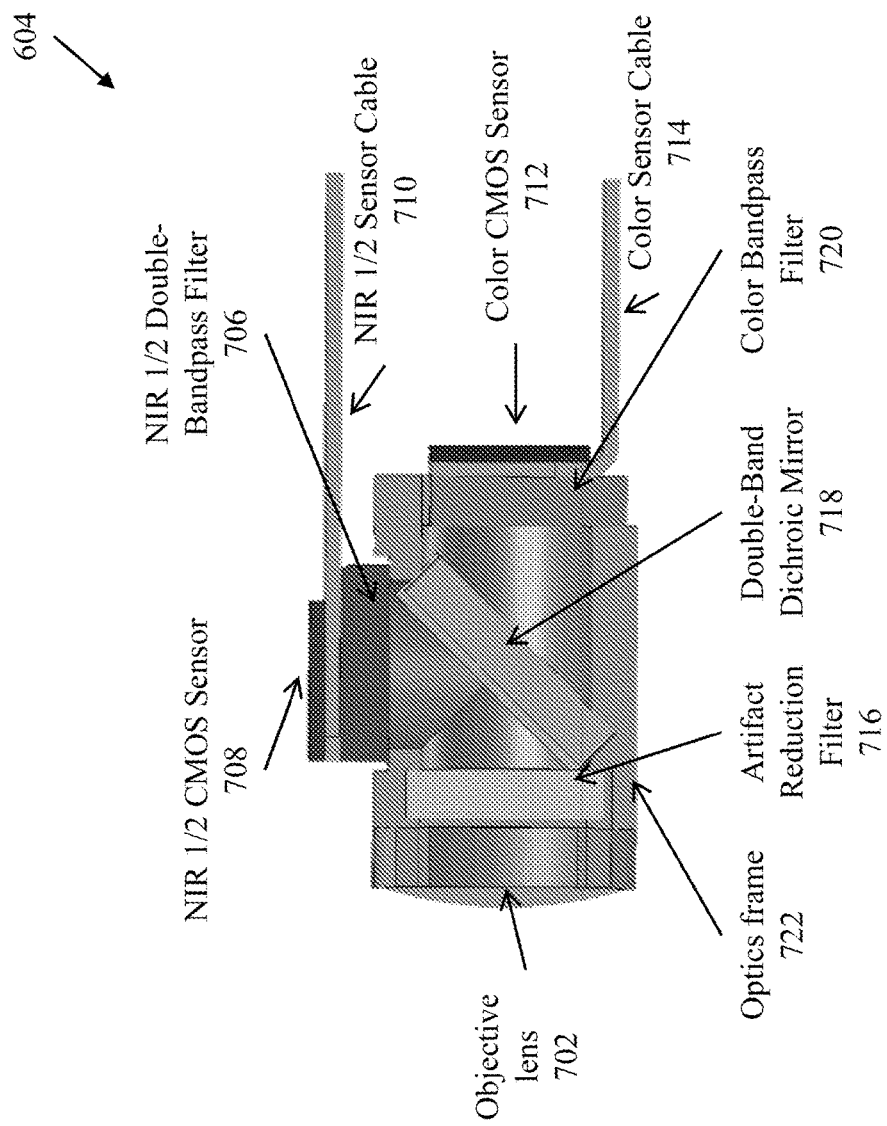
Figure 7C:
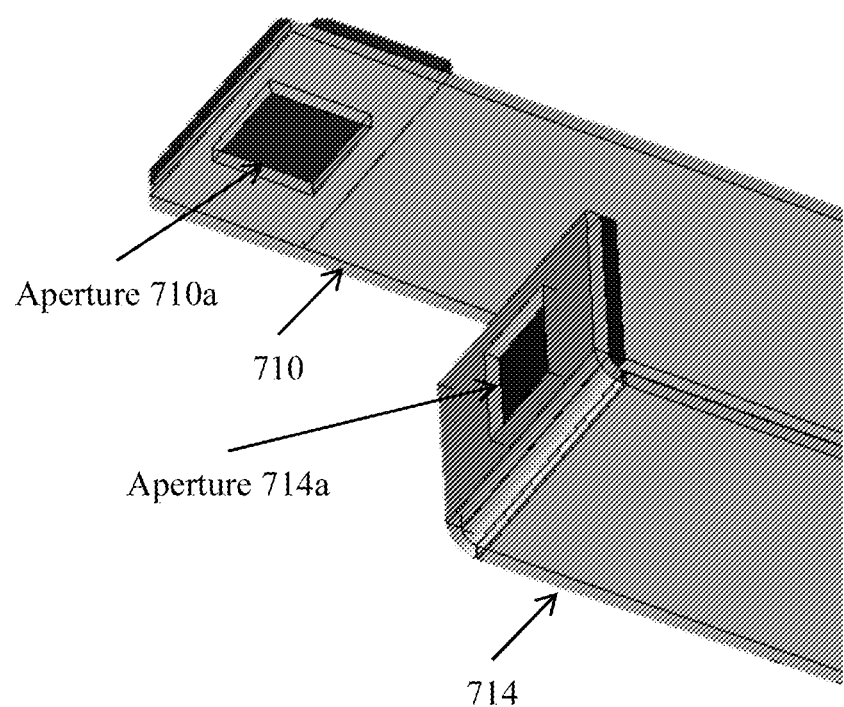

FIGS. 7A-7C illustrate example views of the 2-sensor optical sensor assembly 604, in greater detail. As shown, the 2-sensor optical sensor assembly 604 may include an objective lens 702 and one or more illumination fibers 704 on the tip of the scope, potentially running on opposing sides of assembly 604. Behind the lens 702 may be an artifact reduction filter 716, followed by a double-band dichroic mirror 718 located at an angle that directs captured NIR light towards an NIR CMOS sensor 708 and captured visible light through a color bandpass filter 720 and towards a color CMOS sensor 712, as shown particularly in FIG. 7B. Each of these two CMOS sensors 708 and 712 may have its own CMOS sensor cable 710 and 714, respectively. Each of the components shown in FIG. 7B may also be housed within an optics frame 722 sized to fit at the tip of a scope. In some embodiments, as shown in FIG. 7C, the CMOS sensor cables 710, 714 may have square apertures 710a, 714a, respectively, cut into their end so that the sensing side of the image sensor points towards the light. This is necessary because the CMOS sensors 708, 712 are bare dies that require bonding to pads that are on the sensing side.

Figure 8:
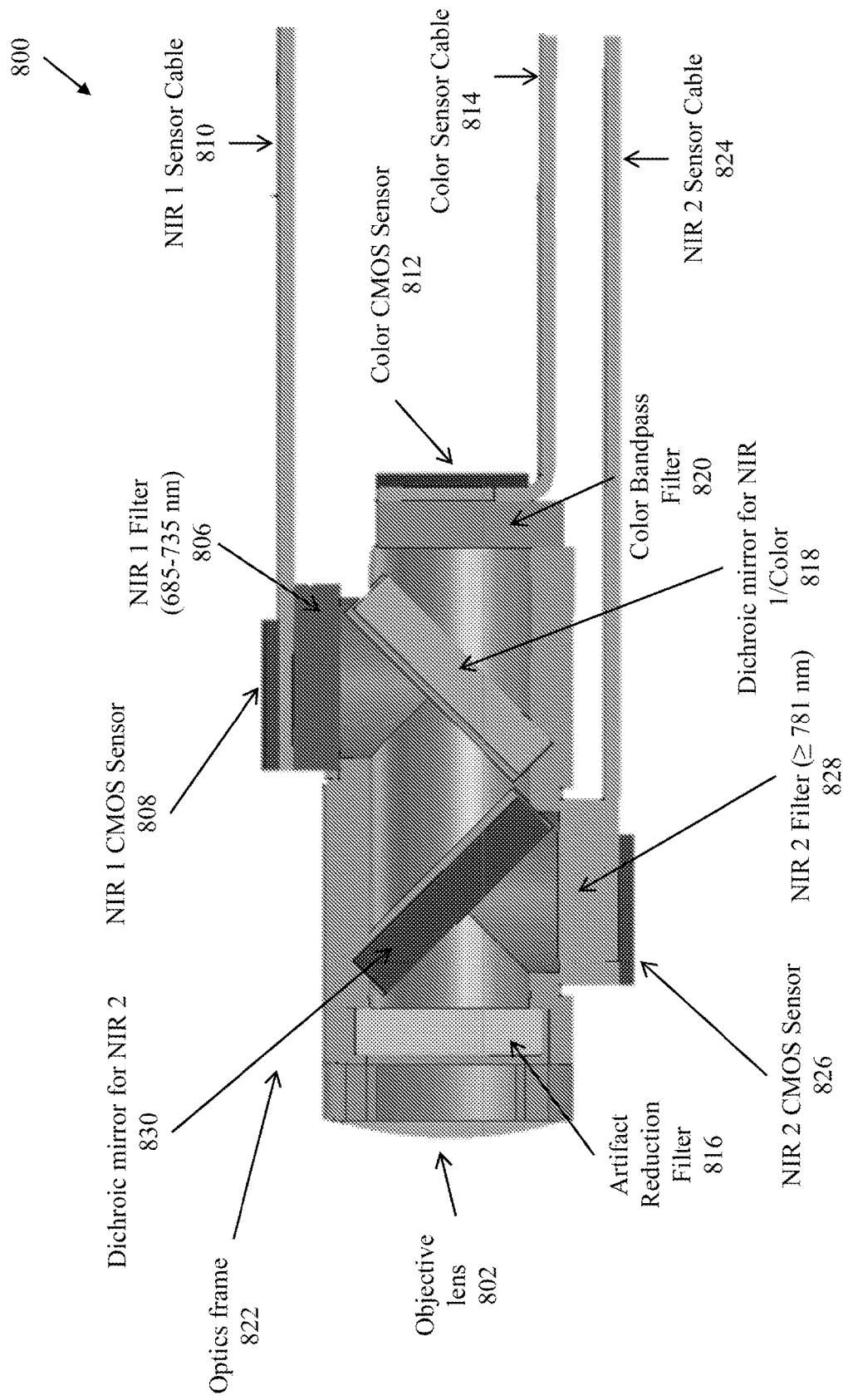
FIG. 8 illustrates an example cross-sectional view of an optical sensor assembly for a 3-sensor scope.

FIG. 8 illustrates an example cross-sectional view of an optical sensor assembly 800 for a 3-sensor scope, in further embodiments. In the 3-sensor case, the optical sensor assembly 800 may comprise an optical frame 822 in which three CMOS sensors are housed: a color CMOS sensor 812, a first NIR CMOS sensor (NIR 1) 808, and a second NIR CMOS sensor (NIR 2) 826, which are connected to sensor cables 814, 810, and 824, respectively. To capture different NIR wavelengths using the two separate sensors 808, 822, each of the two sensors may have its own corresponding filter. For example, NIR 1 filter 806 for the range of 685-735 nm may be located in front of NIR 1 CMOS sensor 808. Similarly, an NIR 2 filter 828 for wavelengths greater than 781 nm may be located in front of the NIR 2 CMOS sensor 826.

To route the captured light towards the CMOS sensors 812, 808, and 826, the 3-sensor optical sensor assembly 800 may include two dichroic mirrors 818 and 830. Notably, a first dichroic mirror 830 may direct light captured by objective lens 802 and filtered by artifact reduction filter 816 towards the NIR 2 CMOS sensor 826 and a second dichroic mirror 818 may direct the captured and filtered light towards the NIR 1 CMOS sensor 808. The captured light may also pass through both dichroic mirrors 830, 818 for reception by the color CMOS sensor 812.

Figure 9A:
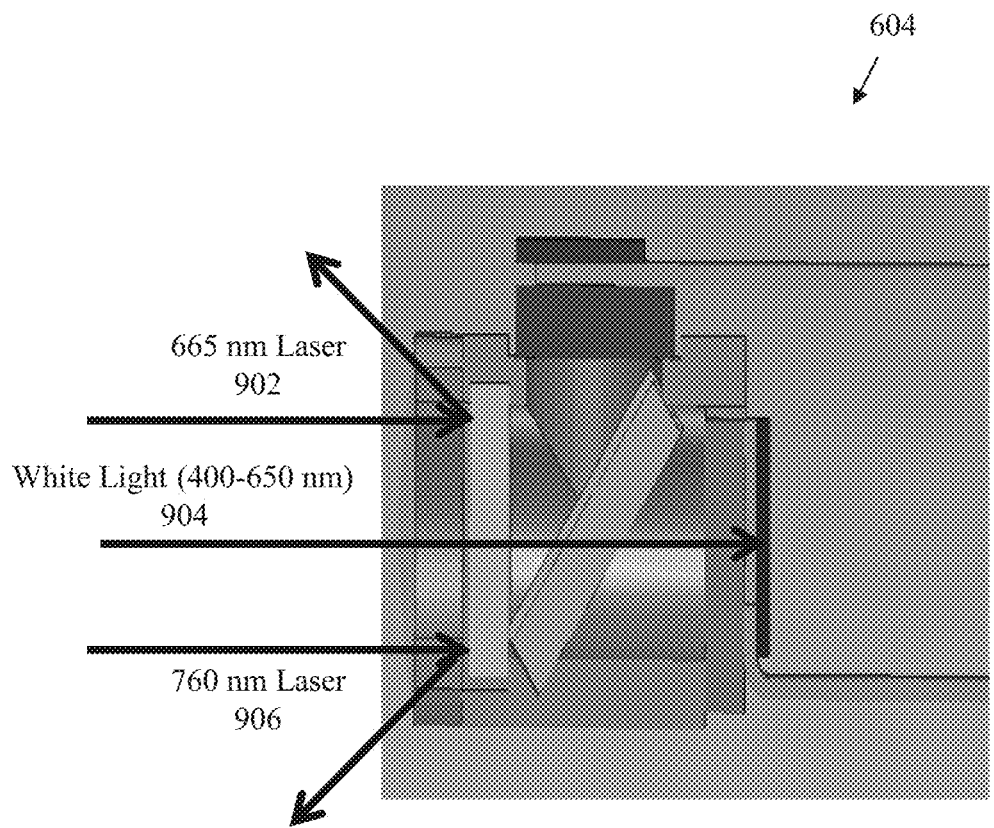
FIGS. 9A-9E illustrate example scope light paths.
Figure 9B:
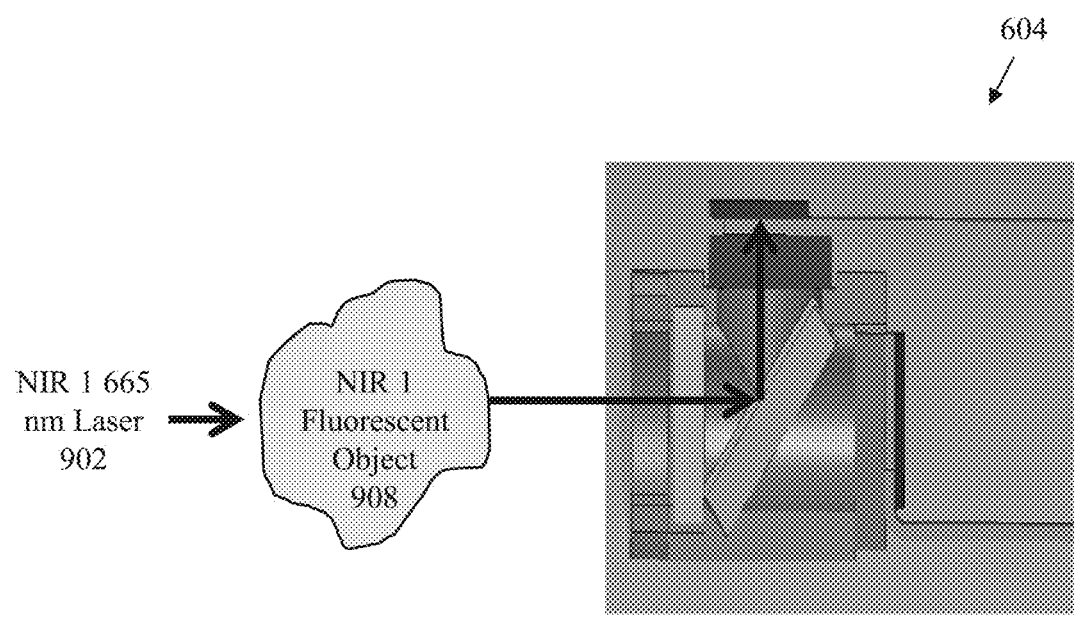
Figure 9C:
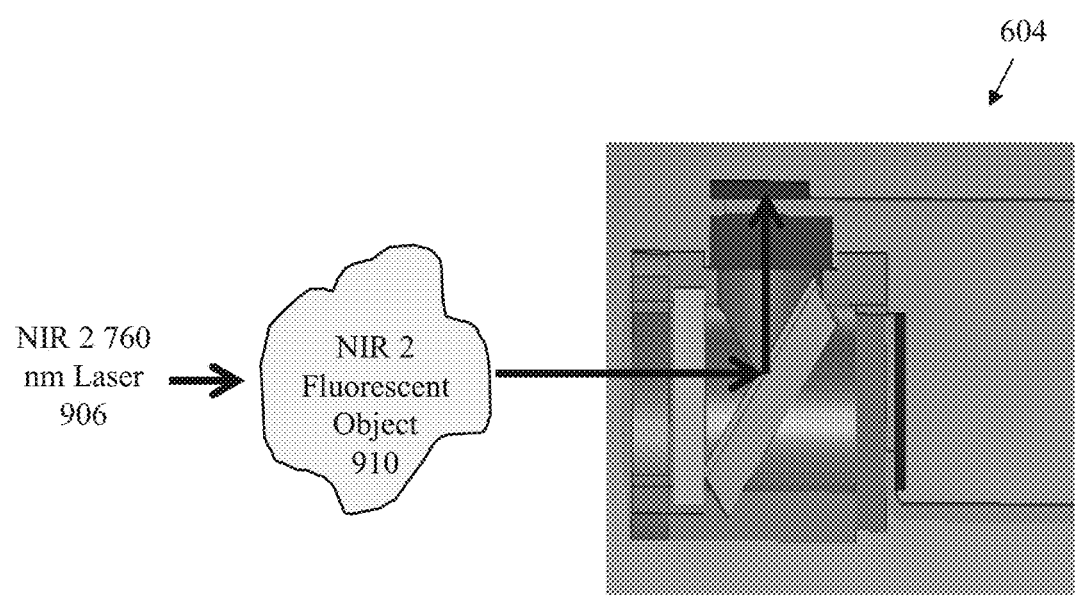
Figure 9D:
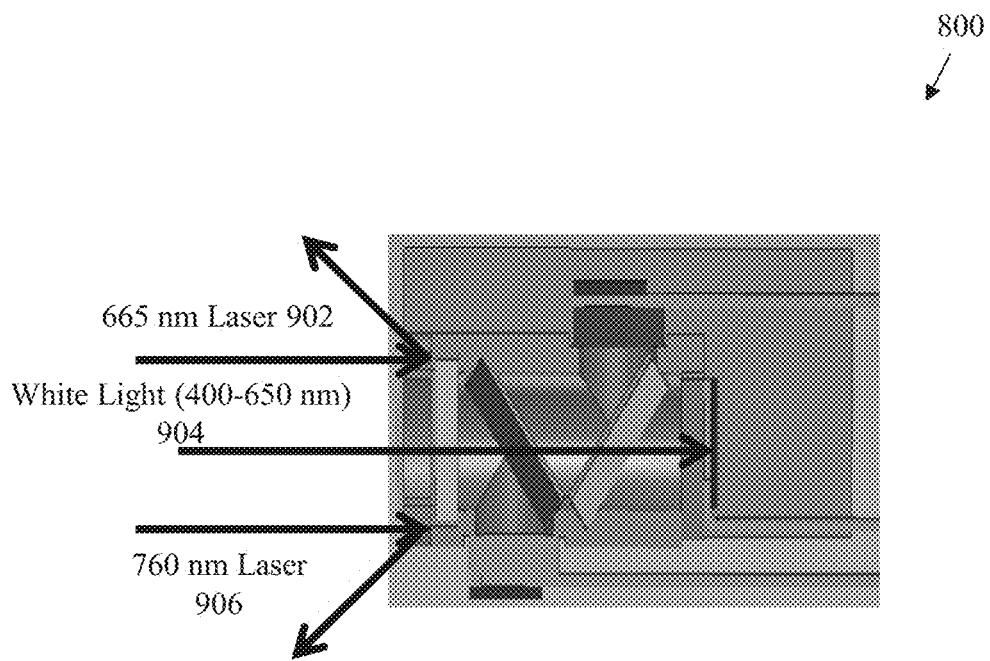
Figure 9E:
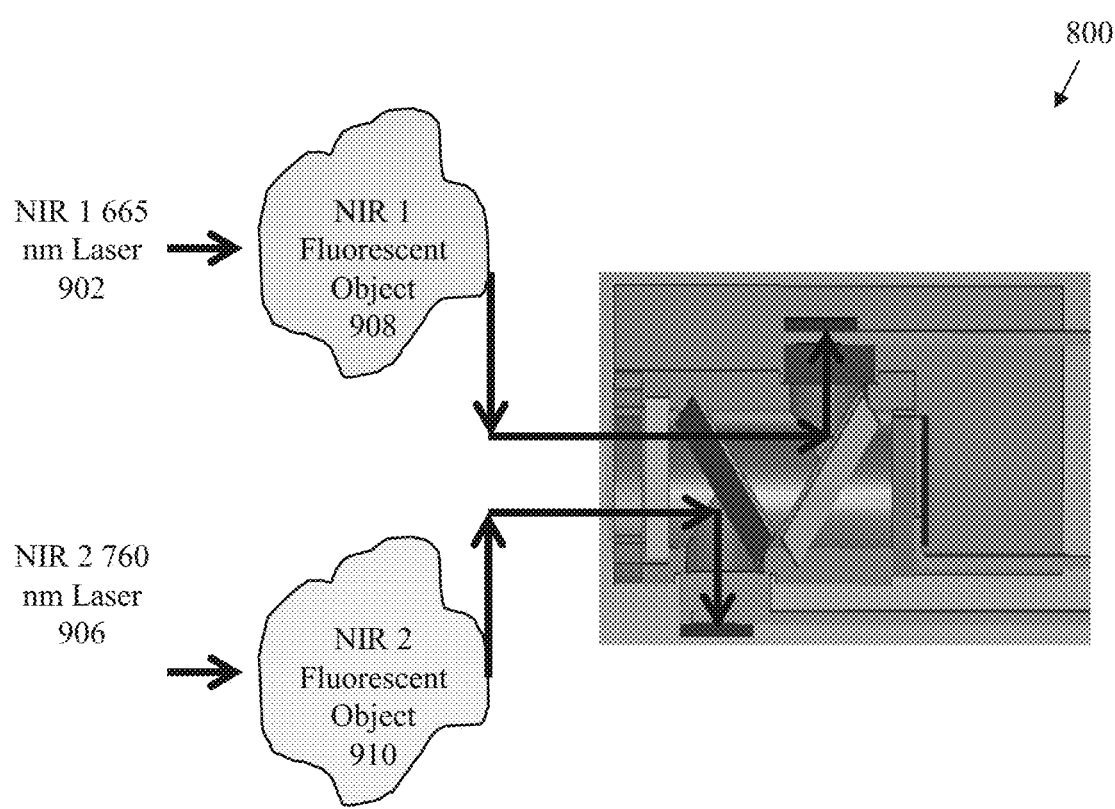

FIGS. 9A-9E illustrate the lightpaths for the 2-sensor and 3-sensor configurations, in various embodiments. In FIGS. 9A-9C, assume that a 2-sensor assembly is used, such as assembly 604. FIG. 9A illustrates an example of the rejection and transmission of the illumination light. Notably, the 665 nm laser light 902 and the 760 nm laser light 906 may be rejected, while white light 904 is allowed through. FIG. 9B illustrates an example of NIR channel 1 fluorescence whereby the 665 nm laser light 902 is used to fluoresce object 908, which is then captured by the NIR sensor of assembly 604. FIG. 9C illustrates a similar example whereby NIR channel 2 fluorescence is captured by shining laser 906 onto object 910. FIGS. 9D-9E illustrate similar examples, but for the case of a 3-sensor configuration, such as with sensor assembly 800. More specifically, FIG. 9D shows the same lights 902-906 as in FIG. 9A, resulting in a similar mode of color video imaging. In FIG. 9E, like in FIGS. 9B-9C, lights 902 and 906 may be used to fluoresce objects 908-910, respectively, allowing for the capture of NIR fluorescence on both NIR channels.

Figure 10:
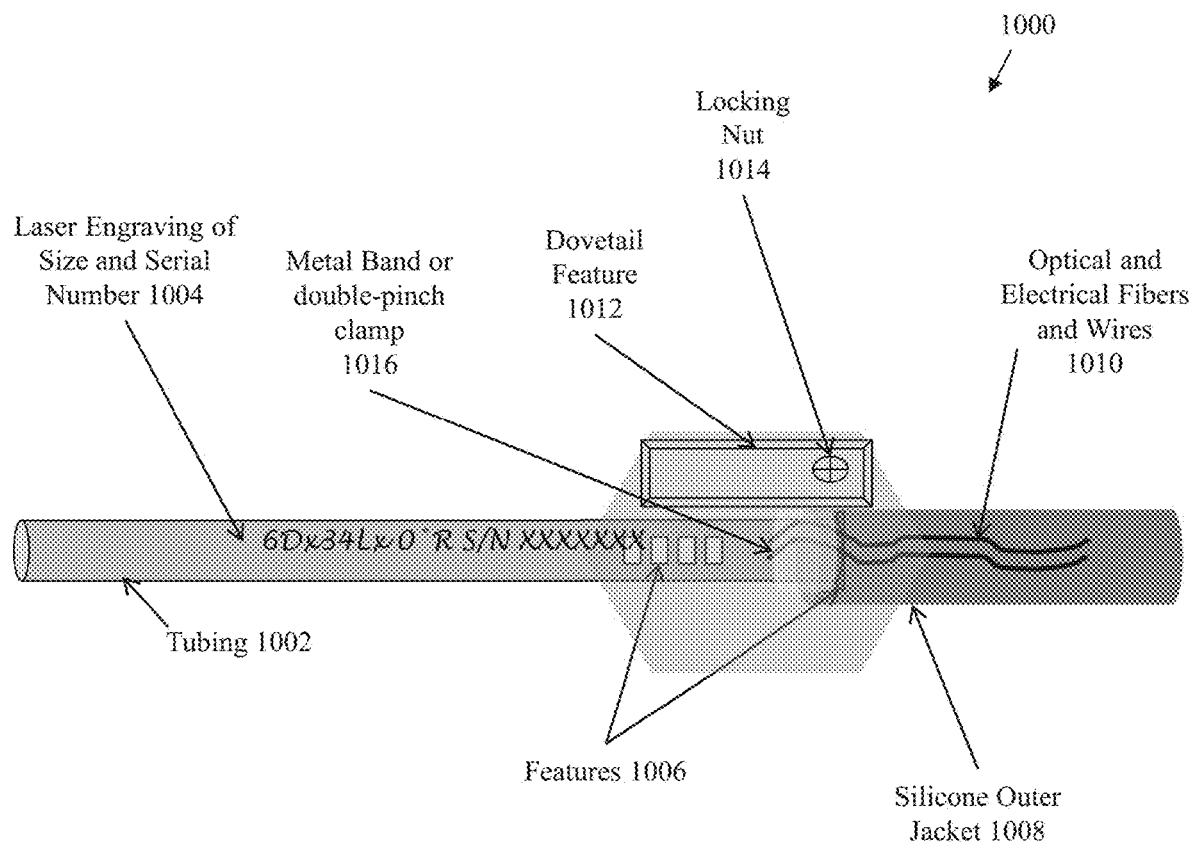
FIG. 10 illustrates an example scope handle.

FIG. 10 illustrates an example handle 1000 for an imaging scope, in various embodiments. As shown, tubing 1002 may extend from the handle and may be 6 mm D or 10 D stainless steel on which a size and serial number 1004 may be engraved. To help retain tubing 1002, features 1006 may also be placed onto tubing 1002, such as cuts or one or more flanges. Ideally, a silicone outer jacket 1008 for fibers and electronics 1010 would be over-molded right onto handle 1000. In some embodiments, a dovetail feature 1012 and ¼"-20 locking nut 1014 for easy mounting may be included, as well as a metal band or double-pinch clamp 1016.

Figure 11:
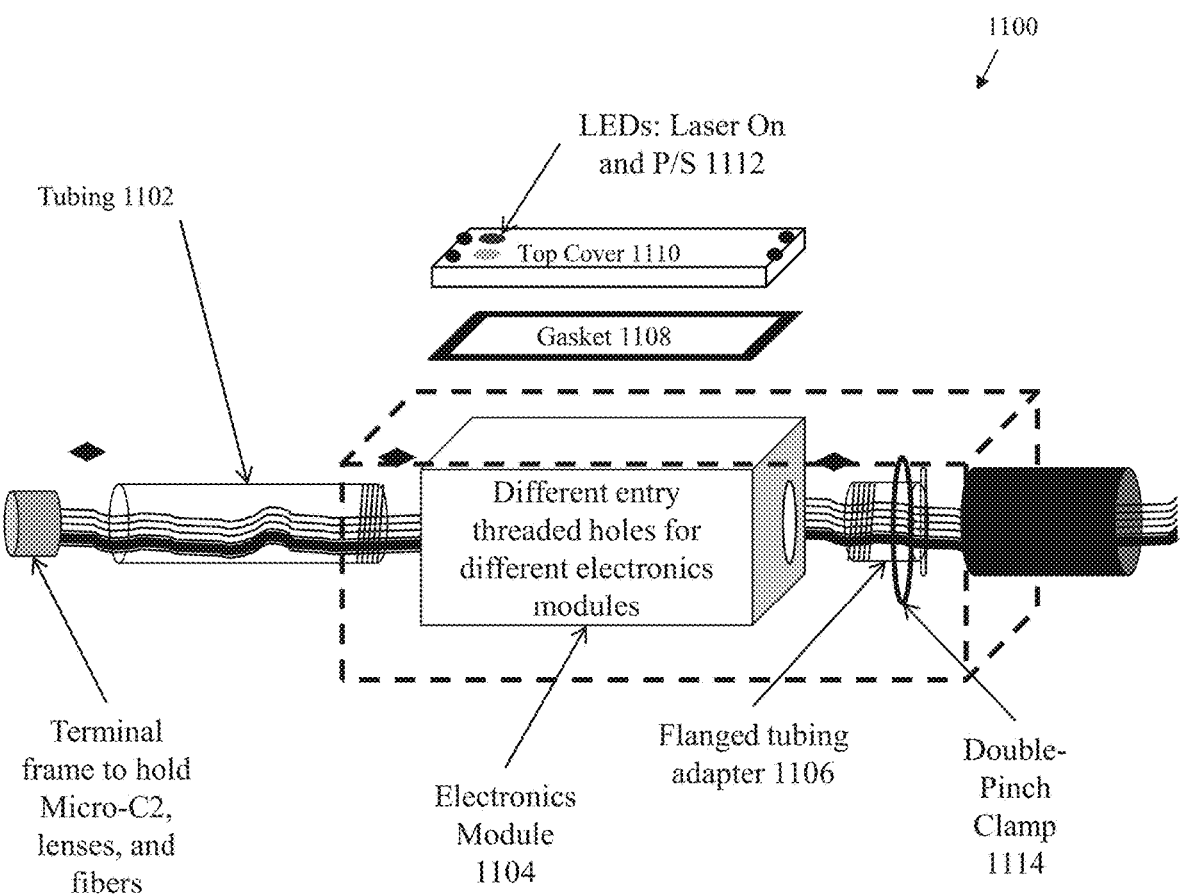
FIG. 11 illustrates an example scope housing assembly.

FIG. 11 illustrates an example scope housing assembly 1100, in various embodiments. As shown, a multi-piece design can be employed, for ease of manufacturing, with any or all of the following features:

Turn down end of long stainless steel (SS) tubing 1102 to screw into electronics module 1104.

Laser engrave long SS tubing 1102 prior to assembly

Different module openings of module 1104 for different sized long tubing but same output size to silicone umbilical Rather than using over-molding, a tight fit, 3-D printed silicone cover that snaps into place could also be used.

Figure 12B:
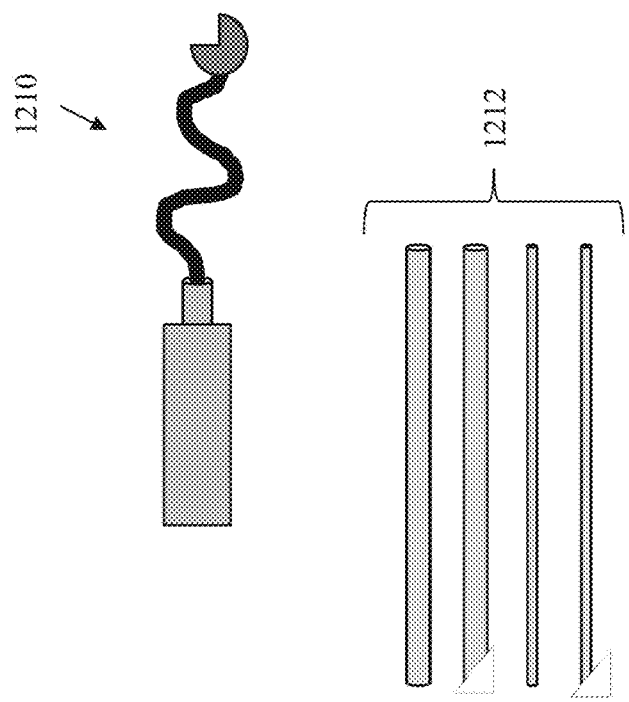
FIGS. 12A-12B illustrate example one-piece and multi-piece scopes.
Figure 12A:
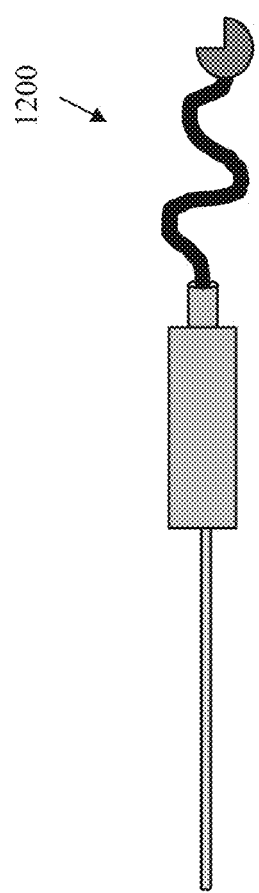

FIGS. 12A-12B illustrate example one-piece and multi-piece scopes 1200 and 1210, respectively, in various embodiments. In the one piece design, a taper can be added to the cart-end of the umbilical cord, so that the diameter of the fiber bundle can be smaller. The working channel will also need to be a straight-shot to back of device, and optical and electrical components can be offset, as needed. In the multi-piece design, plastic fibers and a single silica fiber could be used, as well as POE. Similar to the one-piece cases, a taper can be added to the cart-end of the grip, to allow for smaller diameter fiber bundles. In the multi-piece case, disposable ends 1212 can be employed, with different, selectable diameters.

Figure 13:
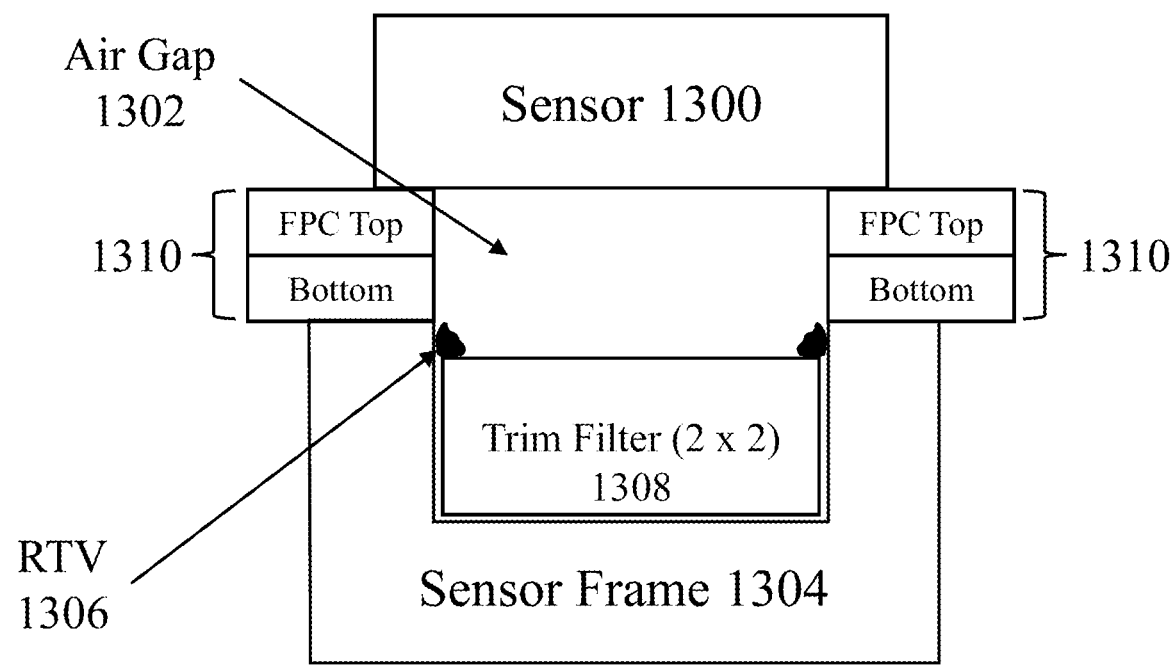
FIG. 13 illustrates an example OVT sensor.

FIG. 13 illustrates an example CMOS sensor 1300 that can be used herein, according to various embodiments. As shown, the sensor 1300 may be mounted to a sensor frame and a double-layered FPC/FFC cable 1310 employed, which does the following:

1.) Creates the air gap 1302 necessary to protect the sensor;
2.) Creates a flat surface on which to slide on the sensor frame 1304 for positioning without any risk of damaging sensor 1300;
3.) If designed correctly, increases tolerance for RTV 1306 so that it does not ride high above the filter 1308.

The following are the materials from which to choose for the frame 1304 to which the optics, mirrors, filters, and sensor mount:

TABLE 3

| Material | Coefficient of Thermal Expansion | Coefficient of Thermal Conductivity | Hardness | Yield Strength | Density |
|---|---|---|---|---|---|
| Aluminum - Bead blast black anodized | 22 | 215 | 2.75 | 35 | 2.7 |
| Steel - Black oxide | 12 | 51 | 4.25 | 205 | 8.0 |
| Stainless Steel - Black oxide | 15 | 17 | 7.5 | 205 | 7.7 |
| Nickel - Bead blast black nickel | 13 | 91 | 4 | 58 | 8.9 |
| Copper - Bead blast black nickel | 16 | 400 | 3 | 70 | 9.0 |
| Brass | 18.5 | 109 | 3.5 | 135 | |
| Plastics | 80 | 0.2 | <1 | n/a | 0.9 |

Because thermal expansion on these small size scales is so important, as is mechanical stability, nickel might be the best overall choice, in some cases. Notably, nickel has a 40% lower coefficient of thermal expansion than aluminum, 2-4× more thermal conductivity than steels, yet the same hardness as steel. Nickel is particularly appealing that UV LIGA and other MEMS techniques result in nickel outer coatings so if regular machining or laser micro-machining look promising but are low throughput, MEMS could also be used, which has higher accuracy. Of course, any of the above materials could be selected, as desired (e.g., aluminum may be more desirable based on price or availability, etc.).

It will be appreciated that the above functionality is merely illustrative, and that other dyes, imaging hardware, and optics may be usefully deployed with the imaging systems described herein. For example, an endoscopic tool may employ a still-image imaging system for diagnostic photography within a body cavity. Or any of the imaging systems may be used as described above with excitation and/or emission wavelengths in the far-red spectrum. Through minor adaptations that would be clear to one of ordinary skill in the art, the system could be configured to image two or more functions (i.e., tumor and blood flow) at the same time that a visible light image is captured by associating each function with a different dye having a different emission wavelength. Non-medical applications exist for the imaging system. For example, dyes in a solution form may be sprayed on a mechanical component to identify oxidation, surface defects, or the like. Dyes could also be used to track gas, steam, or air flow through a pressurized system, and in particular to identify leaks around fittings and valves. These and other arrangements and adaptations of the subject matter discussed herein are intended to fall within the scope of the invention.

Accordingly, the techniques herein allow for fluorescence imaging using a micro, CMOS-based optical sensor assembly located at the tip of a scope. In some aspects, the techniques provide for the use of range-finding spots in an imaging system that are invisible to the user, either by hiding the imaging window used to measure the particular wavelength of the range-finding spots or by constantly alternating between imaging and range-finding with the optical imaging device, but only displaying the imaging information. In doing so, this creates a situation whereby the imaging "workflow" is not interrupted by the range-finding functions.

As will be appreciated, the above examples are intended only for the understanding of certain aspects of the techniques herein and are not limiting in nature. While the techniques are described primarily with respect to a particular device or system, the disclosed processes may be executed by other devices according to further implementations. For example, while the techniques herein are described primarily with respect to medical and research imaging, the techniques herein are not limited as such and can be adapted for use in other industries, as well. Further, while the techniques herein are described particularly in the context of NIR fluorescence imaging systems, the range-finding techniques herein are not limited as such and can be applied within any number of different types of optical imaging systems.

The foregoing description has been directed to specific embodiments. It will be apparent, however, that other variations and modifications may be made to the described embodiments, with the attainment of some or all of their advantages. For instance, it is expressly contemplated that the components and/or elements described herein can be implemented as software being stored on a tangible (non-transitory) computer-readable medium (e.g., disks/CDs/RAM/EEPROM/etc.) having program instructions executing on a computer, hardware, firmware, or a combination thereof. Accordingly, this description is to be taken only by way of example and not to otherwise limit the scope of the embodiments herein. Therefore, it is the object of the appended claims to cover all such variations and modifications as come within the true spirit and scope of the embodiments herein.

What is claimed is:
1. An imaging system, comprising:
an endoscope tube having a distal tip portion defining a tip end;
an optical sensor assembly located at the distal tip portion of the endoscope tube, wherein the optical sensor assembly comprises a single near-infrared (NIR) complementary metal—oxide—semiconductor (CMOS) sensor and a visible light CMOS sensor;
first and second NIR laser channels provided at least in part by a single fiber bundle that is in communication with corresponding first and second NIR lasers and the single NIR CMOS sensor;
a double-bandpass filter located in the distal tip portion and in optical communication with the single NIR CMOS sensor;
an objective lens located in the distal tip portion of the endoscope tube; and
an artifact reduction filter located in the distal tip portion of the endoscope tube between the objective lens and the single NIR CMOS sensor and the visible light CMOS sensor, wherein from a distal end of the distal tip portion proximally along a longitudinal axis of the endoscope tube, first the objective lens is arranged, then the artifact reduction filter, then the optical sensor assembly comprising the single NIR CMOS sensor and the visible light CMOS sensor,
wherein the objective lens and the artifact reduction filter are adjacently positioned in the distal tip portion of the endoscope tube,
wherein the optical sensor assembly is configured to direct NIR light exiting the artifact reduction filter towards the NIR CMOS sensor and configured to direct visible light exiting the artifact reduction filter towards the visible light CMOS sensor, and
wherein the imaging system is configured to sequentially toggle operation of the first NIR laser and the second NIR laser and then collect corresponding signals from the single NIR CMOS sensor.

2. The imaging system of claim 1, further comprising a color bandpass filter in optical communication with the visible light CMOS sensor.

3. The imaging system of claim 1, wherein from the distal end of the distal tip portion proximally along a longitudinal axis of the endoscope tube the single NIR CMOS sensor is in front of the visible light CMOS sensor.

4. The imaging system of claim 1, wherein the artifact reduction filter is configured to reject light in a wavelength range of one or more light sources and allow white light and NIR fluorescence light to pass.

5. The imaging system of claim 1, wherein optical elements of the optical sensor assembly are configured to direct NIR wavelengths exiting the artifact reduction filter in a first optical path towards the single NIR CMOS sensor and configured to direct visible light in a second optical path towards the visible light CMOS sensor.

6. The imaging system of claim 1, wherein the single NIR CMOS sensor is configured to generate NIR images during a surgical procedure and the visible light CMOS sensor is configured to generate visible light images during the surgical procedure, and p1 wherein the imaging system further comprises a controller configured to shift the NIR images to color switch the NIR images into a visible light range at a defined wavelength or wavelengths that is in a color or colors that is/are distinct from visible light colors of the visible light images.

7. The imaging system of claim 6, further comprising a display, wherein the controller is configured to superimpose the visible light images and the shifted NIR images to generate superimposed images and provide the superimposed images to the display.

8. The imaging system of claim 7, wherein the controller is further configured to adjust a frame rate of the visible light images and/or the NIR images to generate the superimposed images.

9. An endoscopy system, comprising:
an endoscope tube having a distal tip portion defining a tip end;
an optical sensor assembly located at the distal tip portion of the endoscope tube, wherein the optical sensor assembly comprises a single near-infrared (NIR) complementary metal—oxide—semiconductor (CMOS) sensor and a visible light CMOS sensor;
first and second NIR laser channels configured with a common single fiber bundle, and in communication with corresponding first and second NIR lasers and the single NIR CMOS sensor;
a double-bandpass filter located in the distal tip portion and residing optically upstream of the single NIR CMOS sensor;

an objective lens located in the distal tip portion of the endoscope tube; and an artifact reduction filter located in the distal tip portion of the endoscope tube, wherein from a distal end of the distal tip portion proximally along a longitudinal axis of the endoscope tube, first the objective lens is arranged, then the artifact reduction filter, then the single NIR CMOS sensor, then the visible light CMOS sensor, p1 wherein the optical sensor assembly is configured to direct NIR light exiting the artifact reduction filter towards the single NIR CMOS sensor and configured to direct visible light exiting the artifact reduction filter towards the visible light CMOS sensor, and p1 wherein the endoscopy system is configured to sequentially toggle operation of the first NIR laser and the second NIR laser and collect corresponding signals from the single NIR CMOS sensor.

10. The endoscopy system of claim 9, wherein the artifact reduction filter is configured to reject light in a wavelength range of one or more light sources and allow white light and NIR fluorescence light to pass.

11. The endoscopy system of claim 9, further comprising a color bandpass filter in optical communication with the visible light CMOS sensor.

12. The endoscopy system of claim 9, wherein the single NIR CMOS sensor is configured to generate NIR images during a surgical procedure and the visible light CMOS sensor is configured to generate visible light images during the surgical procedure, and wherein the endoscopy system further comprises a controller configured to shift the NIR images to color switch the NIR images into a visible light range at a defined wavelength or wavelengths that is in a color or colors that is/are distinct from visible light colors of the visible light images.

13. The endoscopy system of claim 12, further comprising a display, wherein the controller is configured to superimpose the visible light images and the shifted NIR images to generate superimposed images and provide the superimposed images to the display.

* * * * *

UNITED STATES PATENT AND TRADEMARK OFFICE
CERTIFICATE OF CORRECTION

| | |
|---|---|
| PATENT NO. | : 11,744,439 B2 |
| APPLICATION NO. | : 17/840748 |
| DATED | : September 5, 2023 |
| INVENTOR(S) | : John V. Frangioni |

It is certified that error appears in the above-identified patent and that said Letters Patent is hereby corrected as shown below:

In the Claims

Column 14, Line 36, Claim 6: Please correct "procedure, and p1 wherein" to read --procedure, and wherein--

Column 15, Line 9, Claim 9: Please correct "sensor, p1 wherein" to read --sensor, wherein--

Column 15, Lines 13-14, Claim 9: Please correct "sensor, and p1 wherein" to read --sensor, and wherein--

Signed and Sealed this
Fourteenth Day of November, 2023

*Katherine Kelly Vidal*
Katherine Kelly Vidal
*Director of the United States Patent and Trademark Office*